(12) United States Patent
Banko

(10) Patent No.: US 8,641,658 B1
(45) Date of Patent: Feb. 4, 2014

(54) SURGICAL HAND PIECE WITH DUAL LUMEN WORK TIP

(75) Inventor: William Banko, Armonk, NY (US)

(73) Assignee: Surgical Design Corporation, Armonk, NY (US)

( * ) Notice: Subject to any disclaimer, the term of this patent is extended or adjusted under 35 U.S.C. 154(b) by 786 days.

(21) Appl. No.: 12/215,315

(22) Filed: Jun. 26, 2008

(51) Int. Cl.
*A61B 17/20* (2006.01)

(52) U.S. Cl.
USPC .................................... 604/22; 604/173

(58) Field of Classification Search
USPC .......................... 604/22, 27, 28, 35, 118, 178
See application file for complete search history.

(56) References Cited

U.S. PATENT DOCUMENTS

| | | | |
|---|---|---|---|
| 6,282,442 B1 * | 8/2001 | DeStefano et al. | 604/21 |
| 2002/0022796 A1 * | 2/2002 | Lawrence et al. | 604/27 |
| 2002/0161326 A1 * | 10/2002 | Sussman et al. | 604/35 |
| 2003/0176791 A1 * | 9/2003 | Rabiner et al. | 600/439 |

* cited by examiner

*Primary Examiner* — Kevin C Sirmons
*Assistant Examiner* — Brandy S Lee
(74) *Attorney, Agent, or Firm* — Leason Ellis LLP

(57) ABSTRACT

A surgical hand piece has a source of ultrasonic energy provided to a connecting body having a first passage with one end to receive fluid from a first source and the other end at the connecting body distal end. A work tip has first and second tubes each having at least one opening at its distal end and the proximal end of one or both of the tubes connected to the connecting body distal end to receive the ultrasonic energy and to selectively receive or discharge fluid from either the first or second source as controlled by a valve.

17 Claims, 4 Drawing Sheets

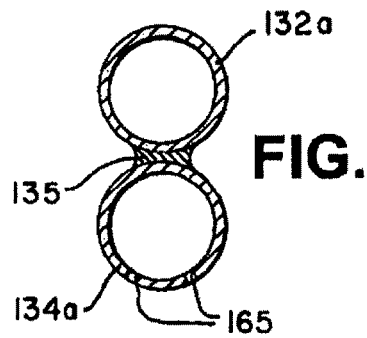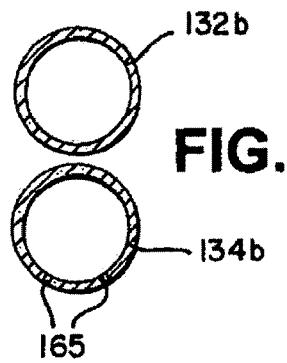
FIG. 3A  FIG. 3B
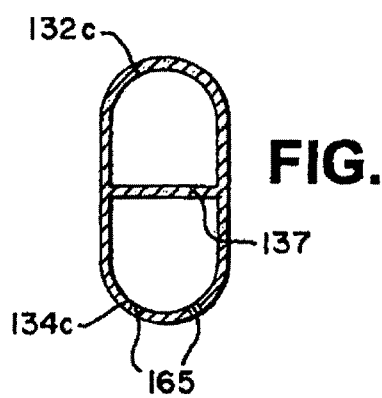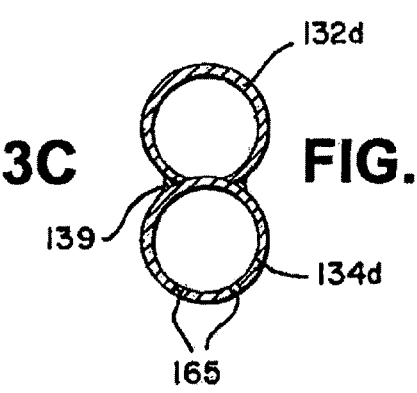
FIG. 3C  FIG. 3D
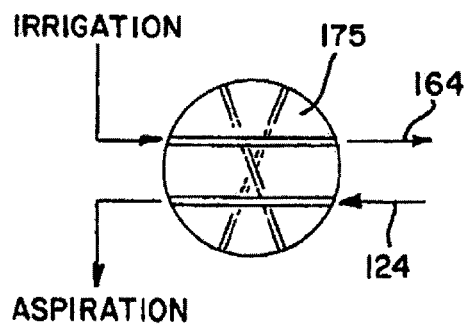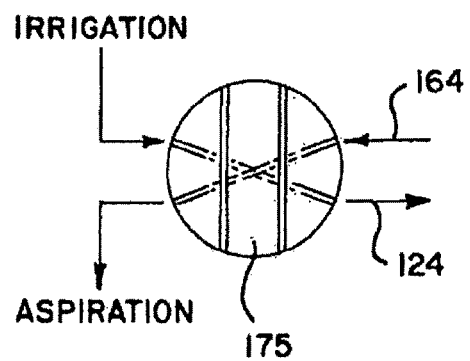
FIG. 4A  FIG. 4B

SURGICAL HAND PIECE WITH DUAL LUMEN WORK TIP

BACKGROUND OF THE INVENTION

The use of ultrasonic instruments in surgical applications is well known. One widely used type of instrument is an ultrasonic hand piece that is used in ophthalmic applications, such as in the removal of cataracts from the eye by phacoemulsification.

FIG. 6 depicts one such type of prior art ultrasonic hand piece as shown in U.S. Pat. No. 4,504,264. There is a housing 10 of, for example, of plastic or metal, within which is supported a transducer means 11 for generating mechanical vibrations upon excitation with an alternating-current electrical signal. The transducer 11 is shown as a magnetostrictive transducer with an electrical coil 12 wound about each leg of a stack of metal laminations so that longitudinal mechanical vibrations are produced. The transducer also can be of the piezoelectric type. There is a connecting body 16 of, for example, titanium, having a reduced diameter distal end portion, which also can be an attached separate portion. The connecting body forms an acoustic impedance transformer for conveying the longitudinal vibrations of the transducer 11 for application to an operative tool or working tip 14 connected to the distal end of the connecting body 16.

The work tip 14 is at least partially external of the housing 10. It is connected, such as by a screw thread, to the narrowed distal end of the connecting body 16 so as to be coupled to the transducer 11 to be longitudinally vibrated thereby. The working tip 14 is an elongated, hollow tip of a suitable metal, such as titanium, that is capable of supporting ultrasonic vibrations and has a distal end of a desired shape to be placed against the tissue to be removed. The work tip 14 has a base portion 15 in threaded engagement with the distal end of the connecting body 16. The tip 14 can be interchanged by use of the screw threads.

The distal end of the tip 14 is shown surrounded by a sleeve 17, such as of silicone, whose proximal end 18 is supported in threaded engagement on a reduced diameter end of the housing 10. If desired, the proximal end of sleeve 17 can be engaged more proximally along the length of the housing 10. The connecting body 16 has two elastomeric O-rings 19, 20 on its outer surface. These provide fluid-tight seals between the connecting body 16 and the internal wall of housing 10. A plurality of screws 51 are shown disposed around the axis of the housing 10 for preventing longitudinal displacement (other than vibration) or rotational movement of the vibratory structure within the housing and also for radial centering of the vibratory structure within the housing. Other types of conventional mounting arrangements can be used.

The hand piece also illustratively has electrical input terminals 40, 41 for applying a suitable electrical signal to the magnetostrictive transducer 11. Cooling water is shown provided inside the housing 10 from an inlet 42 to an outlet 43 and within a chamber between O-ring 19 and a grommet 50 for circulation around the transducer and connecting body. This is not always necessary and is not used in most present day hand pieces The sleeve 17 around the tip 14 forms a first fluid passage 21 between the tip 14 and the sleeve for irrigation fluid. An inlet 22 is provided on the housing or sleeve distally of the O-ring 20 for supplying the irrigation fluid to the passage 21 from a fluid supply (not shown).

A passage 23 is formed through the connecting body 16 that is in communication with a central passage 25 of the work tip 14. An outlet 24 on the housing or sleeve receives a suction (aspiration fluid) force that is applied to the passage 23 in the connecting body and the central passage 25 in the work tip. A chamber 31 is formed between the spaced O-rings 19, 20 on the body 16 and the housing 10, with which the aspiration force communicates. Thus the aspiration force is from the source, into the chamber 31 between the O-rings, through the passage 23 in the connecting body and the passage 25 in the work tip 14. Tissue that is emulsified by the work tip is aspirated from the operating site by the aspiration flow force.

Other apparatus (not shown) for the hand piece includes a suction pump for producing the aspiration fluid (suction), a treatment fluid supply (irrigation fluid, such as a liquid), an oscillator for applying an electrical signal to the vibratory structure and control apparatus therefore. All of these are of conventional construction.

Considering now the operation of the hand piece of FIG. 6, when an electrical signal having a frequency of, for example, 40,000 cycles is applied to the coil 12 around the magnetostrictive transducer 11, the transducer 11 vibrates longitudinally at 40,000 cycles per second, thereby vibrating the connecting bodies 13, 16 and the working tip 14. Treatment fluid is supplied through inlet 22 and fluid passage 21 to bathe the tissue in the operating site region around the working tip 14. Suction force fluid is applied through inlet 24 and passage 23 to the working tip 14 passage 25 to withdraw the tissue fragmented by the work tip.

Instruments of the type described above are often used in cataract surgery in which the eye lens is removed from the eye capsule and an intra-ocular lens (IOL) is then implanted. In such a procedure before the IOL is implanted it has been found to be desirable to cleanup lens substance and lens epithelial cells (LEC's) in the capsular bag and to remove them. Doing this procedure provides a more stable and long-term fixation for certain types of IOL's in the capsular bag. One manner of accomplishing the cleanup is to use a combination of irrigation of the capsular bag interior with a liquid together with the application of low power ultrasonic energy. This dislodges the unwanted cells and substances so that they can be removed from the capsular bag by the aspiration fluid flow.

In such a cleanup procedure it is advantageous if the flow of the irrigation liquid can be made more directional than would be possible using the hand piece with the outer sleeve through which the liquid flows and exits from around the work tip that produces the ultrasonic energy. While it is possible to use a separate lumen or probe that conveys only the irrigation liquid, this has a disadvantage in that the surgeon would have to keep inserting and withdrawing the ultrasonic work tip and irrigation probe from the eye.

Accordingly a need exists for a surgical hand piece that can provide both ultrasonic energy to emulsify tissue, cells and other substances which are aspirated by an aspiration fluid and irrigation liquid that can be applied to part of the operating site being cleaned in a more directional and controlled manner.

BRIEF DESCRIPTION OF THE INVENTION

In accordance with the invention a surgical hand piece is provided that can perform all of the functions of emulsification of tissue and other substances by ultrasonic energy, aspiration of such tissue and substances, and also provide a more directed liquid irrigation of a site that is being worked on.

The invention provides a surgical hand piece that has a novel work tip having a dual lumen construction. The work tip is effectively a unit of two tubes or sections of two tubes. Hereafter the term "tube" refers to a full tube or a section of a tube with each such tube or section having its own lumen. Where sections of tubes are used at least a portion of such sections are integrated along a common surface. One of the tubes receives the ultrasonic energy from the hand piece and its lumen forms the aspiration passage through which the emulsified tissue and other substances are removed. This tube can have any desired shape at its working end and any desired shape of aspiration opening. The irrigation liquid flows through the other tube and its end can have any number of openings or ports in any desired pattern to direct the flow of the irrigation fluid.

The novel work tip permits switching of the tubes between aspiration and irrigation functions so that the surgeon has a work tip with different types of openings for both irrigation and aspiration functions. In different embodiments of the invention, both of the tubes of the work tip can be supplied with ultrasonic energy and either one used for aspiration or irrigation.

The hand piece of the invention has numerous advantages. For example, the need for an infusion sleeves within which the irrigation liquid flows is eliminated. An infusion sleeve is a separate item that needs to be attached to the instrument hand piece. This means that such sleeves have to be designed and manufactured for a particular hand piece. Also, the sleeves are subject to wear and tear and other complications. The elimination of the need for an infusion sleeve from the surgical hand piece has economic advantages in that there are fewer parts to deal with. There also is a surgical benefit in that it eliminates the need for the surgeon to remove a work tip from the operating site, such as the eye, and to insert a separate work tip or tips having irrigation/aspiration (I/A) capability, to perform special procedures such as cortical and lens epithelial cleanup.

BRIEF DESCRIPTION OF THE DRAWINGS

Other objects and advantage of the present invention will become more apparent upon reference to the following specification and annexed drawings in which:

FIGS. 3A, 3B, 3C and 3D are cross-sectional views showing various forms of integrated work tip;

FIGS. 4A and 4B are schematic views of a valve arrangement to control switching between irrigation and aspiration functions for the tubes of the work tip;

DETAILED DESCRIPTION OF THE INVENTION

Figure 1:
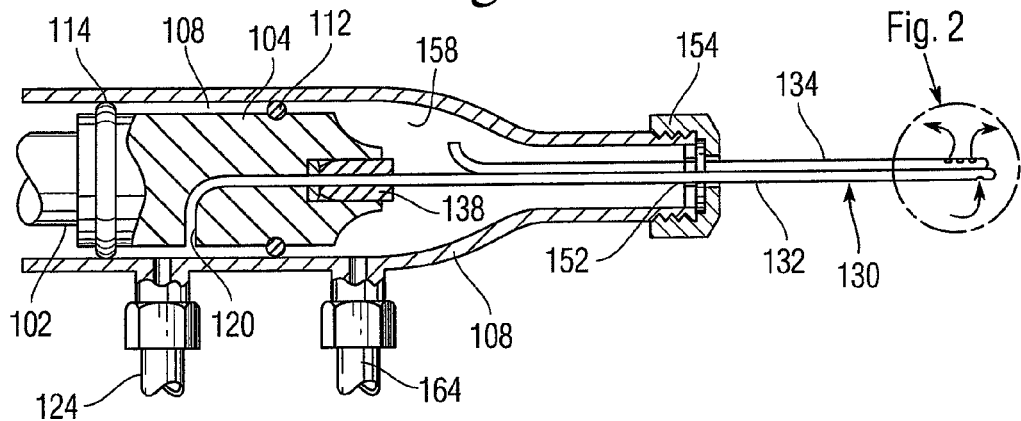
FIG. 1 is a plan view, partly in cross section, of one embodiment of the surgical hand piece of the invention.
Figure 6:
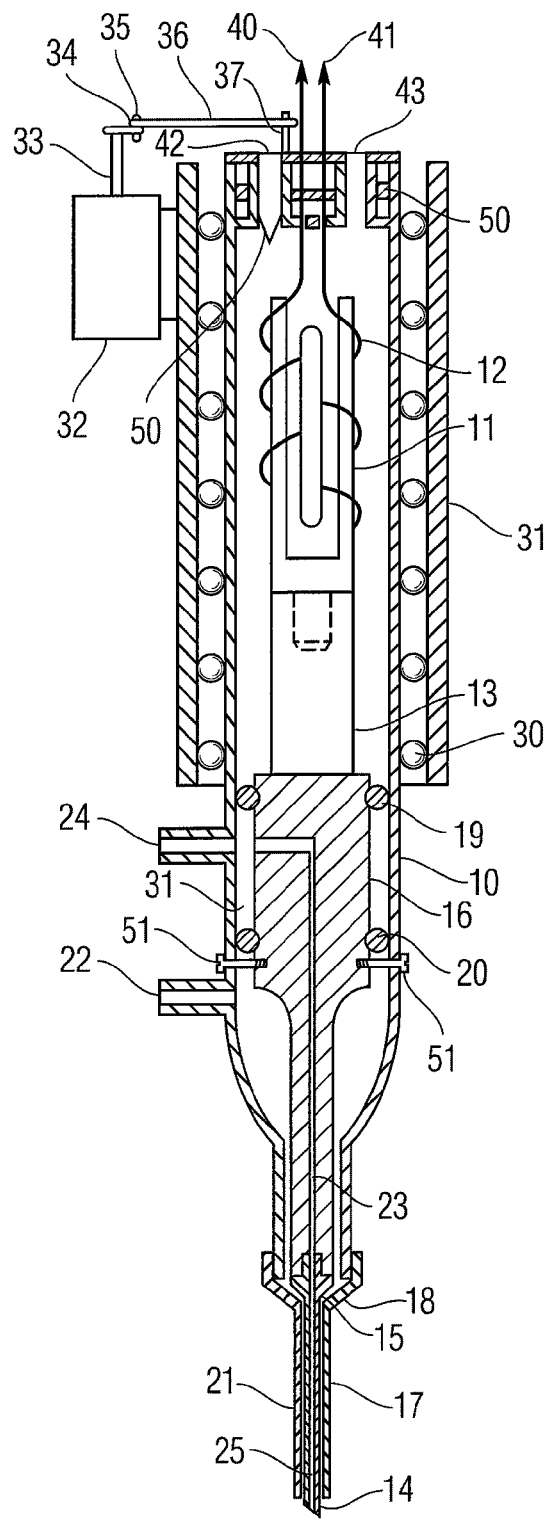
FIG. 6 is a view in cross-section of the prior art type of surgical hand piece.

FIG. 1 shows a first embodiment of the hand piece of the invention. It uses a number of the components of the prior art type of hand piece described above with respect to FIG. 6. The source of the electro-mechanical energy is shown schematically by reference number 102 and can be either the electro-magnetic type as described or the piezoelectric type. It is preferred, and is conventional, that the output power of the source 102 can be controllably varied to set the ultrasonic power at the work tip distal end.

Connected to the source 102 is the connecting body 104 within a housing 108. A pair of O-rings 112 and 114 spaced apart around the connecting body 104 and engaging the inner surface of the housing form a first chamber 118. The first chamber 118 receives aspiration fluid force flow from a line 124 that is connected to a suitable source such as a peristaltic pump. It is preferred that the fluid supplied by such a source, actually a negative (suction) pressure, be controllable. A flow passage 120 is formed in the connecting body 104 that communicates with the first chamber 118 and extends to the reduced diameter distal end of the connecting body 104.

A second chamber 158 is formed between the O-ring 112 and the distal end of the housing 108. This chamber receives fluid from a line 164 that is connected to a suitable source, such as a bag of saline solution or a liquid supply having a pump. Here also, it is preferred that the volume and pressure of the fluid be controllable. The proximal end of a work tip 130 extends through the distal end of the housing 108. A flange hub 152 is connected to an intermediate point of the work tip and the flange abuts against the distal end of the housing 108 and is held against it by a threaded collar 154. This forms a fluid tight seal at the distal end of the housing and seals the second chamber 158.

The work tip 10 is a unit of two tubes or tubular sections 12 and 134. The two tubes can be of any of the types illustratively shown in FIGS. 3A-3D and described below. As illustratively shown, the proximal end of the work tip 130 first tube 132 has a coupling 138 that is threaded into the distal end of the connecting body 104. This places the lumen of the first tube 132 in communication with the passage 120 in the connecting body 104. The tube 132 will also be provided with ultrasonic energy from the source 102 through the connecting body 104. At the proximal end of the work tip 130 there is a second tube 134, which is open, located in the housing second chamber 158 and in communication with any fluid in this chamber. With this arrangement, there is fluid flow to or from each of the tubes 132 and 134 of the integrated work tip 130. That is, aspiration, flow or liquid flow can be provided to the proximal end of the first tube 132 through the line 124, the housing first chamber 118 and passage 120 in the connecting body 104. Similarly, fluid flow can be provided to the proximal end of the second tube 134 from the line 164 and the second housing chamber 158.

Figure 1A:
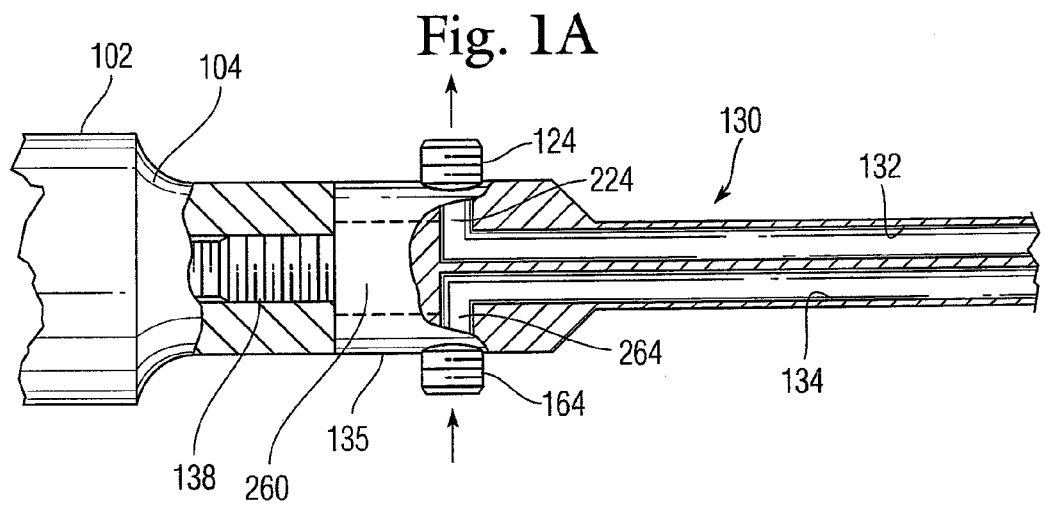
FIG. 1A is a plan view, partly in cross section, of another embodiment of the surgical hand piece of the invention.

FIG. 1A shows a further embodiment in which there is no flow passage in the connecting body. Here, the proximal end of the work tip 130 is a generally cylindrical hub 135 that receives the proximal ends of the tubes 132 and 134. The tubes can be any of the types described below with respect to FIGS. 3A-3D. The proximal end of the hub 135 is of reduced diameter so that it can be attached such as by threads 138 with threads in a recess of the distal end of the connecting body 104 whose proximal end is connected to the source of ultrasonic energy. The hub 135 has a respective passage 224 and 264 to the lumen of each of the tubes 132 and 134. The aspiration and irrigation fluids are supplied over the lines 124 and 164 through the hub passages directly to the lumens of the two tubes. The lines 124 and 164 can be inserted directly into the hub passages 224 and 264. A housing (not shown) of a suitable shape would be provided over the energy source 102 and the connecting body 104. In this embodiment, both tubes 132, 134 receive the ultrasonic energy. As described below, the fluids supplied to the two tubes can be switched by using a control valve.

The work tip of FIG. 1A has an advantage in that there is no fluid flow through the connecting body 104 or any part of the instrument other than the work tip 130 itself. Therefore, it is the only part of the instrument that can become contaminated if the patient being operated on has a malady such as "mad cow" disease. Only the work tip has to be sterilized after each use of the instrument or the work tip can be treated as a "disposable" and a new work tip used each time that the instrument is used.

Figure 2:
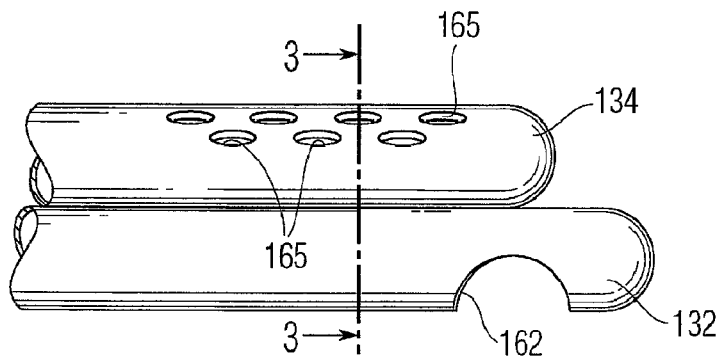
FIG. 2 is an enlarged view of the ends of the work tip.
Figure 5:
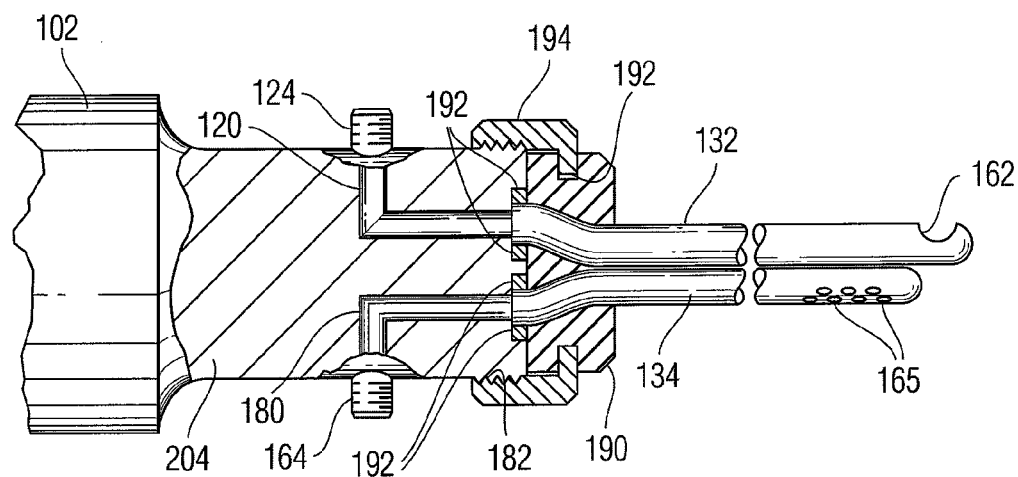
FIG. 5 is a view, partly in cross-section, of another embodiment of surgical hand piece of the invention.

FIG. 2 shows an illustrative example of the distal ends of the two tubes 132 and 134 of the work tip 130. The proximal end of the tubes are disposed as shown in FIGS. 1 and 1A or in another embodiment as shown in FIG. 5, or by any suitable arrangement such that ultrasonic energy from the transducer and aspiration fluid is coupled to the proximal end of at least one of the tubes and the proximal end of at least one tube can receive the irrigation fluid. In this example the first tube 132 is intended to be connected to receive the ultrasonic energy from the source 102 and has a scooped, or concave shaped, opening 162 near its distal end to receive the emulsified tissue that is produced by vibrations of the free end of the tube. The opening 162 can be of any desired shape and size and also can be at the extreme distal end of the tube. The second tube 134 has at least one and preferably a plurality of openings 165 through which an irrigation liquid can flow to exit to the operating site. The number of openings 165 and their pattern can be selected as desired. There can be one or more rows along the tube length. The openings 165 in tube 134 preferably are oval (elliptical) in shape as shown. Oval shaped openings 165 allow for both good dispersion of the irrigation fluid and a large area for aspiration of cells and substances dislodged by the irrigation liquid. The openings 165 also can have the standard circular hole configuration. As explained below, the hand piece of the invention provides for switching of the functions to be performed by the two tubes. That is, either tube can be used to perform the irrigation function or the aspiration function.

FIGS. 3A, 3B, 3C and 3D show cross-sections of tubes that can be used for the work tip 130. In FIG. 3A two fully circular tubes 132a and 134a are joined together at the area 135, such as by welding or brazing, to form a unitary structure. The joining 135 can be continuous or spaced along the lengths of the two tubes. When two complete tubes are used for the work tip they do not necessarily have to be connected together along their lengths as shown in FIG. 3A since each tube has its own lumen and does not need any part in common with the other tube to have fluid flow therein. An arrangement of two separate tubes 132b and 134b is shown in FIG. 3B. A unitary structure work tip is formed by using a hub or a similar element to hold the two tubes together as shown in FIGS. 1, 1A and FIG. 5.

In FIG. 3C two half tube sections 132c and 134c are connected to a common central wall 137 to form a unitary structure. Here an overall somewhat elliptical tube can be divided into the two tube sections and then joined to the center common wall 137. In FIG. 3D there is a fully circular tube 134d on top of which a part of a circular tube section 132d is joined at 139 along its length making the work tip a unitary structure. When two tube sections are used to form the work tip the proximal ends are modified (not shown) to have the appropriate shape, such as fully circular, so as to be able to perform its function such as coupling to the connecting body to receive ultrasonic energy and to receive aspiration and irrigation fluid. The distal ends also are modified to provide fluid flow to the aspiration and irrigation openings.

It should be understood that the two tubes 132 and 134 can be of different diameters and shapes in addition to the more symmetrical arrangements shown in the drawings. Also, the tubes can be of any suitable material, such as titanium or any suitable material which can withstand the stress of vibration and both can be of the same material, or they can be of different materials. It also may be desirable to make one of the tubes, for example the one to which the irrigation fluid is usually applied, of a plastic material such as TEFLON. While a tube of plastic material will not be able to vibrate if it receives ultrasonic energy it still can be used to perform both the aspiration and irrigation functions depending upon which fluid is supplied to it. Further, the two tubes 132 and 134 can be of different lengths.

FIGS. 4A and 4B schematically show a valve arrangement for the supply lines 124 and 164. There is a valve 175 that receives one input from an irrigation liquid source, such as a bag of a saline solution using gravity feed or from a liquid source under controlled pressure and volume. The valve second input is from an aspiration source, such as a peristaltic pump, of controlled force or pressure. In FIG. 4A the valve 175 is in a position such that there is irrigation liquid flow is to line 164 meaning that there will be liquid in the second housing chamber 158 to be provided to the second tube 134 to flow out of its distal end. The aspiration source will be connected to the line 124 so that there will be negative pressure (suction) fluid in the first housing chamber 118 that is provided to the distal end of the first tube 132 through the passage 120 in the connecting body 104. As seen in FIG. 4B, by switching the valve 175 the conditions will be reversed so that there will be aspiration flow on line 164 causing the second tube 134 to perform an aspirating function and liquid flow in line 164 causing the first tube 132 to perform an irrigation function.

FIG. 5 shows another embodiment of the invention for coupling the work tip 130 to the hand piece. The same reference numbers are used for the same components of FIG. 1. Here there are two passages 120 and 180 in the connecting body 204. One end, the proximal end, of passage 120 is in communication with the irrigation fluid input of the supply line 124. The proximal end of passage 180 is in communication with the aspiration fluid of the supply line 164. The distal ends of the two passages 120 and 180 terminate at the distal end of the connecting body 204.

There are threads 182 around the connecting body distal end. A hub 190 is around the proximal ends of the work tip tubes 132 and 134 which are bent so that the proximal ends of their lumens are parallel to the distal ends of the connecting body passages 120 and 180. A collar 194 with internal threads on its open end has its flange end rotatably mounted in a groove 192 in the hub 190. There are mating index pieces, such as mating grooves and ribs or pins (not shown), on the opposing faces of the connecting body 204 distal end and the hub 190 so that the proximal end of the lumen of tube 132 will be aligned with the distal end of connecting body passage 120 and the proximal end of the lumen of tube 134 aligned with the distal end of passage 180. Other types of alignment pieces and markings can be used. When the tubes and connecting body are properly aligned the collar 194 is tightened on the connecting body threads 182 and the lumens at the proximal ends of tubes 132 and 134 will be brought into fluid communication with the distal ends of the connecting body passages 120 and 180. O-rings 192 are provided in the connecting body at the distal ends of passages 120 and 180 to make the communication fluid tight.

In this embodiment of the invention, both of the tubes 132 to 134 receive the ultrasonic energy from the source 102. The valve 175 of FIG. 4 can be used with the hand piece of FIG. 5 to switch the fluid flow from the sources 124 and 164 to the lumens of tubes 132 and 134 of the integrated work tip. Since both tubes 132 and 134 receive ultrasonic energy the emulsification of tissue and its aspiration can take place through either one in addition to each tube being able to supply irrigation liquid through the different types and shapes of openings at the distal ends of the tubes.

In each of the embodiments described a support member can be mounted around the work tip 130 to rest against the eye when the work tip is inserted in the eye. For example, a cannula can be inserted into the incision site and then the work tip 130 is placed into the cannula. This cannula provides thermal insulation at the incision sight in order to protect the eye from any heat generated by the vibration of work tip 130.

The work tips of the invention, such as illustratively shown in FIGS. 1, 1A and 5, can be used with only an irrigation/aspiration (I/A) function. That is, the source of ultrasonic energy can be turned off and only the aspiration and irrigation fluids supplied to the tubes 132 and 134. Here also the valve arrangement of FIG. 4 can be used so that either of the tubes can receive either of the fluids. Thus, the same instrument can be used for the phacoemulsification function while performing irrigation and aspiration as an operation takes place and also only for I/A functions (no ultrasonic energy is used) useful for cleaning the capsular bag as described above. This eliminates the need for the surgeon changing instruments and also provides the surgeon with a work tip having two tubes with different shape openings available for both aspiration and irrigation.

Figure 7:
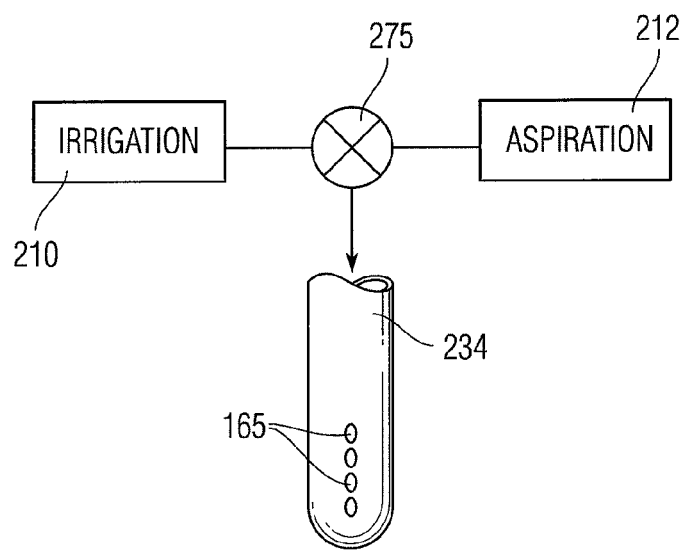
FIG. 7 is a schematic view of a modification of the work tip.

Following the above, only one of the tubes can be used only as an I/A work tip. That is, it does not receive ultrasonic energy. This is shown in FIG. 7 in which the tube 234 follows the general format of the tube 134 of FIG. 2. That is, it has the oval openings 165 along the tube length. It receives either irrigation or aspiration fluid from sources 210 and 212 at its proximal end through a valve 275. The tube 234 can be used alone in the eye capsular bag for the substance and cell cleanup procedure described above. The oval shaped openings 165 allow for both good dispersion of the irrigation fluid and a large area for aspiration of cells and substances dislodged by the irrigation liquid.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the patented scope of the appended claims.

I claim:

1. A surgical hand piece comprising:
a source of ultrasonic energy;
a connecting body having a proximal end connected to said source and a distal end;
a work tip of first and second tubes aligned side by side and adjacent to each other, at least one of said tubes having a proximal end connected to said connecting body distal end and being of a material for the ultrasonic energy from said source to be conveyed to the distal end of said at least one tube,
each said first and second tube having a lumen that is to receive or discharge a fluid at its proximal end from one of first and second sources that are respectively irrigation and aspiration fluids, the lumen of each of said first and second tubes being separate and spaced apart, and each said tube having an opening at its distal end through which the fluid received or discharged at the proximal end of the respective lumen of each said tube exits from or enters the tube, with each said tube distal end opening being separate, independent of, spaced from and without being in communication with the distal end opening for the fluid to exit of the other tube; and
a valve to receive the fluids from both the first and second sources and for switching the received fluids respectively to be supplied to the respective lumen of either one of said first and second tubes, wherein the respective lumen of each of said first and second tubes can receive the fluid from either one of said first and second sources as switched by said valve.

2. The surgical hand piece as claimed in claim 1 wherein said opening at the distal end of said first tube has a concave shape.

3. The surgical instrument as claimed in claim 1 wherein said second tube has a plurality of openings of oval shape at its distal end.

4. The surgical instrument as claimed in claim 1 wherein said first and second tubes are joined together along at lest a portion of their respective lengths.

5. The surgical instrument as claimed in claim 1 wherein said first and second tubes are separate from each other and are connected together at their proximal ends.

6. The surgical instrument as claimed in claim 1 wherein the proximal ends of both said tubes are connected to the distal end of said connecting body and the lumen of each said tube has an opening at its proximal end to directly receive a fluid from one of said first and second sources.

7. The surgical instrument as claimed in claim 1 wherein said connecting body has a passage with one end at an outer surface to receive fluid from a first source and the other passage end at the distal end of said connecting body;
and one of said work tip first and second tubes has its proximal end connected to said connecting body with the lumen of said first tube being in communication with said connecting body passage, and the lumen of said second tube having an opening at its proximal end to receive fluid from a second source.

8. The surgical hand piece as claimed in claim 7 wherein said connecting body has a second passage with one end at an exterior surface of said connecting body to receive fluid from a second source and the other end at the connecting body distal end, and wherein the lumen of said second tube is in communication with said other end of said connecting body second passage.

9. The surgical hand piece as claimed in claim 6 wherein said opening at said first tube distal end has a concave shape.

10. The surgical hand piece as claimed in claim 6 wherein said second tube has a plurality of openings at its distal end through which fluid from said second source is discharged.

11. The surgical instrument as claimed in claim 1 wherein said first and second tubes are connected together as a unit by one of a connection between said tubes and a hub into which said tubes are placed.

12. The surgical handpiece as claimed in claim 1 wherein at least one opening is of oval shape.

13. The surgical handpiece as claimed in claim 1 wherein there are a plurality of openings aligned in a row along the length of one of said tubes.

14. The surgical handpiece as claimed in claim 1 wherein each of said tubes is of a material that can convey ultrasonic energy from its proximal to its distal end.

15. The surgical handpiece as claimed in claim 1 wherein said first and second tubes are connected to each other along the lengths of said first and second tubes.

16. The surgical handpiece as claimed in claim 15 wherein said first and second tubes have a common center wall.

17. A surgical hand piece comprising:
a source of ultrasonic energy;

a connecting body having a proximal end connected to said source and a distal end;

a work tip of first and second tubes aligned side by side and adjacent to each other, at least one of said tubes having a proximal end connected to said connecting body distal end and being of a material for the ultrasonic energy from said source to be conveyed to the distal end of said at least one tube, each said first and second tube having a lumen that is to receive or discharge a fluid at its proximal end from one of first and second sources that are respectively irrigation and aspiration fluids, the lumen of each of said first and second tubes being separate and spaced apart, and each said tube having an opening at its distal end through which the fluid received or discharged at the proximal end of the respective lumen of each said tube exits from or enters the tube, with each said tube distal end opening being separate, independent of, spaced from and without being in communication with the distal end opening for the fluid to exit of the other tube; and a valve to receive the fluids from both the first and second sources and for switching the received fluids respectively to be supplied to the respective lumen of either one of said first and second tubes.

\* \* \* \* \*